United States Patent [19]
Handa et al.

[11] 3,943,771
[45] Mar. 16, 1976

[54] POWDER MATERIAL SAMPLING DEVICE

[75] Inventors: Makoto Handa; Hiromichi Hayashi, both of Sapporo, Japan

[73] Assignee: Snow Brand Milk Products Co., Limited, Sapporo, Japan

[22] Filed: Oct. 15, 1974

[21] Appl. No.: 515,060

[52] U.S. Cl. .................... 73/424; 356/36; 356/244
[51] Int. Cl.² ............................................ G01N 1/20
[58] Field of Search............ 73/422 R, 424; 356/36, 356/244, 245

[56] References Cited
UNITED STATES PATENTS

| | | | |
|---|---|---|---|
| 1,516,896 | 11/1924 | Turner | 356/244 |
| 2,301,815 | 11/1942 | Robinson | 73/424 |
| 2,541,519 | 2/1951 | Jones | 73/424 |
| 3,250,131 | 5/1966 | Jordison | 73/424 |

*Primary Examiner*—S. Clement Swisher

[57] ABSTRACT

Power material adapted to be used in combination with a powder material manufacturing apparatus having a substantially vertical passage for passing manufactured powder material downwardly therethrough, said sampling device including a rotatable disc having a portion projecting into the vertical passage so that a part of the powder material passing through the passage is deposited on the disc and taken out the passage through rotation of the disc.

7 Claims, 2 Drawing Figures

POWDER MATERIAL SAMPLING DEVICE

The present invention relates to a material sampling device and more particularly to a powder material sampling device.

In an apparatus for continuously manufacturing powder milk or the like powder material, it is often required to take out a portion of the powder material for the purpose of testing it in respect of water content and other physical property thereof.

It is therefore an object of the present invention to provide a powder material sampling device which is simple in construction and can be readily accommodated in a powder material manufacturing system.

The above and other objects of the present invention can be accomplished by a powder material sampling device comprising a rotatable disc having a portion projecting into a substantially vertically disposed powder material passage through which powder material is passed downwardly. A portion of the powder material is thus deposited on the projected portion of the disc and taken out of the passage simply by rotating the disc. When it is desired to perform water content test, the sampling device may be combined with an appropriate test equipment such as an ultra-red ray water content measuring device. When such a type of measuring device is combined with the sampling device of the present invention, it is necessary to provide means for leveling off the deposited layer of the powder material.

Figure 1:
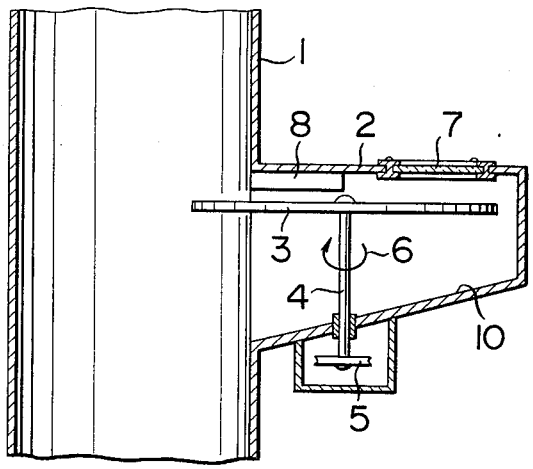
Figure 2:
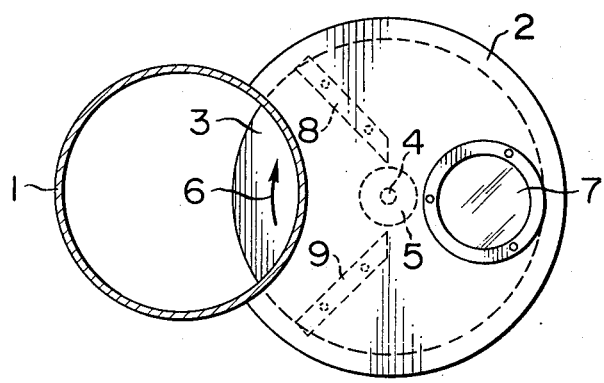

The above and other objects and features of the present invention will become apparent from the following descriptions of the present invention taking reference to the accompanying drawings, in which:

FIG. 1 shows a vertical sectional view of a powder material sampling device in accordance with one embodiment of the present invention; and FIG. 2 is a plan view of the sampling device shown in FIG. 1.

Referring now to the drawings, there is shown a vertical powder material passage 1 which may be connected with a spray drying tower of a powder material manufacturing apparatus (not shown). As shown in FIG. 2, the passage 1 is of a circular cross-section and provided with a sidewardly projecting sampling chamber 2 which is also of a circular cross-section. In the sampling chamber 2, there is provided a rotatable disc 3 which is rotatably supported by a vertical shaft 4. As shown in the drawings, the rotatable disc 3 has a portion projecting into the passage 1. The vertical shaft 4 has a pulley 5 secured to the lower end thereof and driven by a suitable drive source (not shown) so that the shaft 4 is rotated in the direction as shown by an arrow 6 in the drawings. Thus, a part of powder material passing downwardly through the passage 1 is deposited on the portion of the disc 3 projecting in the passage 1, and taken out of the passage 1 by rotating the disc 3. In the illustrated embodiment, the sampling chamber 2 is provided at its upper wall with a transparent window 7 through which physical properties such as water content of the powder material on the disc 3 is measured by using an appropriate device such as an ultra-red ray type measuring device (not shown). When the water content of the powder material is measured through the window 7 by an ultra-red ray type measuring device, it is required to level off the powder material layer on the disc 3. For this purpose, the upper wall of the sampling chamber 2 has a leveling blade 8. The leveling blade 8 has a lower edge which is spaced from the upper surface of the disc 3 by a predetermined distance so that, when the disc 3 is rotated with powder material deposited thereon, the powder material is leveled off when it passes through the spacing between the leveling blde 8 and the disc 3. As shown in FIG. 2, the sampling chamber 2 is further provided at its upper wall with a scraping blade 9 which has a lower edge disposed closely adjacent to the upper surface of the disc 3 so as to scrape off the powder material from the disc 3. Since the sampling chamber 2 has a bottom wall 10 which is inclined downwardly toward the passage 1, the scraped powder material is returned to the passage 1 after the test is performed.

Thus, it will be apparent that, according to the present invention, it is possible to perform a continuous sampling and continuous physical property measurement in a continuous powder material manufacturing apparatus.

Although the present invention has been shown and described with reference to a preferred embodiment, it should be noted that the invention is in no way limited to the details of the illustrated arrangement but changes and modifications may be made without departing from the scope of the appended claims.

We claim:

1. In a powder material manufacturing apparatus having a substantially vertical passage for passing manufactured powder material downwardly therethrough, a sampling device for the powder material which comprises a sampling chamber provided adjacent to the vertical passage, a rotatable disc disposed substantially horizontally in said sampling chamber and having a portion projecting into the passage, and means for rotating said disc so that powder material deposited on the projecting portion of the disc can be taken out of the passage into the sampling chamber through rotation of the disc.

2. Sampling device in accordance with claim 1 in which said sampling chamber has an upper wall provided with a transparent window through which a physical property of the powder material on the disc can be measured.

3. Sampling device in accordance with claim 2 in which means is provided at the upstream side of the window as seen in the direction of rotation of the disc for leveling the powder material deposited on the disc.

4. Sampling device in accordance with claim 3 in which said leveling means is a leveling blade secured to the upper wall of the sampling chamber and having a lower edge spaced from the disc by a predetermined distance.

5. Sampling device in accordance with claim 2 in which means is provided at the downstream side of the window as seen in the direction of rotation of the disc for scraping the powder material from the disc.

6. Sampling device in accordance with claim 5 in which said scraping means comprises a scraping blade secured to the upper wall of the sampling chamber and having a lower edge disposed closely adjacent to the disc.

7. Sampling device in accordance with claim 5 in which said sampling chamber has a bottom wall inclined downwardly toward the passage so that the powder material scraped of the disc is returned to the passage along the bottom wall.

* * * * *

UNITED STATES PATENT AND TRADEMARK OFFICE
CERTIFICATE OF CORRECTION

PATENT NO. : 3,943,771
DATED : March 16, 1976
INVENTOR(S) : Makoto Handa et al

It is certified that error appears in the above-identified patent and that said Letters Patent are hereby corrected as shown below:

--[30]  Foreign Application Priority Data
October 18, 1973  Japan.........117097/1973--

Signed and Sealed this fifteenth Day of June 1976

[SEAL]

Attest:

RUTH C. MASON
Attesting Officer

C. MARSHALL DANN
Commissioner of Patents and Trademarks